United States Patent
Ichikawa et al.

(10) Patent No.: US 6,773,109 B2
(45) Date of Patent: Aug. 10, 2004

(54) OPHTHALMIC PHOTOGRAPHING APPARATUS

(75) Inventors: Naoki Ichikawa, Gamagori (JP); Hikaru Miyabayashi, Toyohashi (JP)

(73) Assignee: Nidek Co., Ltd., Gamagori (JP)

( * ) Notice: Subject to any disclaimer, the term of this patent is extended or adjusted under 35 U.S.C. 154(b) by 4 days.

(21) Appl. No.: 10/127,661

(22) Filed: Apr. 23, 2002

(65) Prior Publication Data

US 2002/0158890 A1 Oct. 31, 2002

(30) Foreign Application Priority Data

Apr. 27, 2001 (JP) ........................................ 2001-133673

(51) Int. Cl.⁷ .............................................. A61B 3/14
(52) U.S. Cl. ..................................................... 351/206
(58) Field of Search ........................ 351/200, 205–208, 351/211, 221, 246; 600/558

(56) References Cited

U.S. PATENT DOCUMENTS

| 5,374,967 | A |   | 12/1994 | Hideshima et al. |
| 5,912,720 | A | * | 6/1999  | Berger et al. ............... 351/206 |
| 5,943,116 | A |   | 8/1999  | Zeimer |
| 6,082,859 | A |   | 7/2000  | Okashita et al. |
| 6,224,212 | B1 | * | 5/2001 | Noda et al. ................. 351/206 |
| 2002/0113939 | A1 | * | 8/2002 | Kitamura .................... 351/200 |

FOREIGN PATENT DOCUMENTS

| JP | 4-327831 |   | 11/1992 |
| JP | A 9-173298 | * | 7/1997 |
| JP | A 11-332832 | * | 12/1999 |
| JP | A 2000-155788 | * | 6/2000 |
| JP | A 2000-189387 | * | 7/2000 |

\* cited by examiner

*Primary Examiner*—Brian L. Casler
*Assistant Examiner*—John R Sanders
(74) *Attorney, Agent, or Firm*—Oliff & Berridge, PLC (57) ABSTRACT

An apparatus for photographing an eye to be examined, which facilitates interpretation of the relationship between a photographed image and a position at which the image has been photographed. The apparatus includes a device for photoelectrically photographing the eye, a device for displaying a photographed image, a first device for storing a template where a plurality of the images are scaled-down and arranged in given positions so that the images appear on a screen of the displaying device, a device for assigning each image to one position for arranging the images in the template, a second device for storing the images and information about where the images have been assigned, in which the images are each associated with their own assignment information, and a display control device for arranging such that one or more of the images appear on the screen, based on the stored images and information.

6 Claims, 5 Drawing Sheets

OPHTHALMIC PHOTOGRAPHING APPARATUS

This application claims priority from Japanese Patent Application No. 2001-133673, filed on Apr. 27, 2001.

BACKGROUND OF THE INVENTION

1. Field of the Invention

The present invention relates to an ophthalmic photographing apparatus for photographing a fundus of an eye to be examined.

2. Description of Related Art

When a fundus is photographed using a fundus camera, a region that can be photographed at a time is part of the fundus. Therefore, when an image of a large part of a fundus is to be obtained, plural sections of the fundus are each photographed while a fixation light (a fixation target) is used to guide a line of sight of an eye to be examined. Then the image thus photographed is stored in an image memory, and is brought up onto a monitor. When the photographed images are displayed, each of the images may appear individually, or a plurality of the photographed images stored in the memory may be scaled down so that they can appear on the same screen to be observed at a glance.

Conventionally, however, a position in which to arrange the scaled-down image to be displayed on the monitor is not associated with a position on the fundus at which the image has been photographed, and the scaled-down images are arranged in accordance with a sequence of storing the photographed images. This has involved a problem of difficulty in interpreting a positional relationship among the images appearing on an at-a-glance screen.

SUMMARY OF THE INVENTION

The present invention has been made in view of the above circumstances and has an object to overcome the above problem and to provide an ophthalmic photographing apparatus capable of facilitating interpretation of the relationship between a photographed image and a position at which that image has been photographed.

To achieve the objects and in accordance with the purpose of the present invention, as embodied and broadly described herein, an ophthalmic photographing apparatus comprises photographing means for photoelectrically photographing the eye; display means for displaying a photographed image; first storage means for storing a template where a plurality of the images are scaled-down and arranged in given positions so that the images appear on a screen of the displaying means; assigning means for assigning each of the images to one of the positions for arranging the images in the template; second storage means for storing the images and information about where the images have been assigned, in which the images are each associated with their own assignment information; and display control means for arranging that one or more of the images appear on the screen of the display means, based on the stored images and their assignment information.

In another aspect of the present invention, an ophthalmic photographing apparatus comprises a photographing optical system for photographing an eye to be examined, having a photoelectric photographic element; a display, which is sometimes called a monitor; a first memory which stores a template where a plurality of the photographed images are scaled-down and arranged in given positions so that the images appear on the display; an input part which inputs a designation signal to designate one of the positions for arranging the images in the template with respect to each of the images; a second memory which stores the images to which the positions in the template have been designated for arranging the images; and a display control part which arranges that the images appear on the display based on the stored images and the positions designated for arranging the images.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
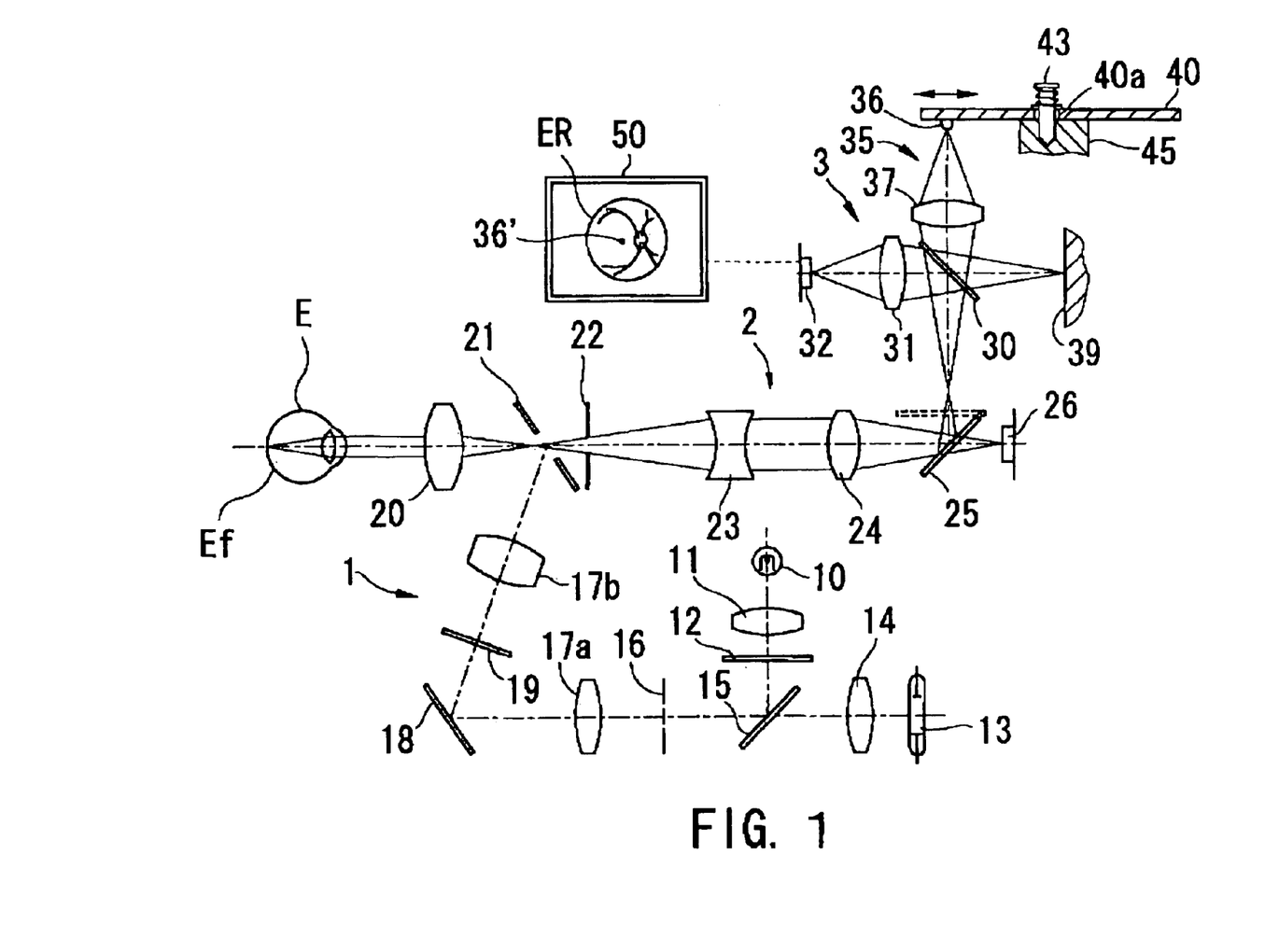
FIG. 1 is a view showing a schematic configuration of an optical system of a fundus camera of non-mydriasis type consistent with a preferred embodiment of the present invention.

A detailed description of a preferred embodiment of a fundus camera consistent with the present invention will now be given referring to the accompanying drawings. FIG. 1 is a view showing a schematic configuration of an optical system in a fundus camera of non-midriasis type. The optical system is provided with an illumination optical system 1, a photographing optical system 2, an observation optical system 3, and a fixation-target presenting optical system 35.

<Illumination Optical System>

Illumination light emitted from a halogen lamp 10 being an illumination light source for observation passes through a condenser lens 11 to be converted into infrared illumination light by an infrared filter 12 having a wavelength-selecting property of transmitting infrared light. Thereafter, the light is reflected by a half mirror 15 and illuminates a ring slit 16 having a ring-shaped aperture. Alternatively, instead of the halogen lamp 10, it may be possible to use such an infrared light source as an infrared LED, which would eliminate the need for the filter 12. Besides, instead of the half mirror 15, it may also be possible to use a dichroic mirror having a wavelength-selecting property of reflecting infrared light and transmitting visible light.

Visible illumination light emitted from a flash lamp 13 being a light source for photographing passes through a condenser lens 14, and is transmitted by the half mirror 15 to be made coaxial with the infrared illumination light, so that the visible illumination light illuminates the ring slit 16.

The illumination light having passed through the slit 16 (ring-slit light) forms an intermediate image in the vicinity of an aperture of an apertured mirror 21 via a relay lens 17a, a mirror 18, a black-dot plate 19 with a small black dot in its center, and a relay lens 17b. The light is then reflected to be coaxial with an optical axis of the photographing optical system 2. Once the illumination light (the ring-slit light) reflected by the mirror 21 forms an image via an objective lens 20 in the vicinity of the pupil of an eye E to be examined, the light is diffused to illuminate a fundus Ef of the eye E uniformly. When entering the lens 20, the illumination light (the ring-slit light) may generate some amount of reflected light which would be detrimental at the time of observing and photographing an image of the fundus Ef. Therefore, it is arranged that the detrimental light should be absorbed by the small black dot provided in the center of the black-dot plate 19.

<Photographing Optical System>

Once the light reflected from the fundus Ef forms an intermediate image of the fundus Ef via the lens 20, the reflected light enters a return mirror 25 through the aperture of the mirror 21, a photographic diaphragm 22, a focusing lens 23 movable in the direction of the optical axis, and an image forming lens 24. The return mirror 25 is placed in a position indicated by solid lines at the time of observation while it is placed in a position indicated by broken lines at the time of photographing. The visible light reflected from the fundus Ef, which is not reflected by the return mirror 25 when the mirror 25 is placed in the position of the broken lines, enters a photographic color COD camera 26 having a sensitivity to the visible region, and then forms an image of the fundus Ef on an imaging surface of the camera 26.

<Observation Optical System>

The observation optical system 3 shares an optical path from the lens 2Q to the return mirror 25 with the photographing optical system 2. (The return mirror 25 is placed in the position of the solid lines except when photographing is performed.) A half mirror 30 has a reflectance larger than a transmittance it has. On an optical path in the direction of reflection from the half mirror 30 are placed a relay lens 31 and an observation CCD camera 32 having a sensitivity to the visible region through the infrared region. The infrared light reflected from the fundus Ef, which is reflected by the return mirror 25 when the mirror 25 is placed in the position of the solid lines, is further reflected by the half mirror 30, and then enters the camera 32 through the lens 31 to form an image of the fundus Ef on an imaging surface of the camera 32. Output from the camera 32 is routed to a color monitor 50 which doubles as a monochrome monitor, so that an image ER of the fundus Ef is displayed on the monitor 50.

<Fixation-target Presenting Optical System>

A fixation-target presenting optical system 35 comprises a point light source 36 as a fixation target and a relay lens 37, and shares the optical path from the return mirror 25 to the lens 20 with the observation optical system 3 via the half mirror 30. The point light source 36 is mounted on a lever 40, so that the lever 40 is manipulated to move the point light source 36 within a plane approximately conjugate with the fundus Ef and the imaging surface of the camera 32. The lever 40, in which an oblong hole 40a is formed, is retained on an enclosure part 45 of the fundus camera by a screw 43 and the like, so that the lever 40 can slide smoothly. Part of the lever 40 extends off the enclosure part 45, permitting an examiner to operate the lever 40 to move the point light source 36, so that he can guide a desired part of the fundus Ef (a line of sight of the eye E).

In addition, a reflecting mirror 39 is provided in the opposite side of the lens 31 across the half mirror 30. The mirror 39 is disposed in a position approximately conjugate with the imaging surface of the camera 32 via the lens 31 and also approximately conjugate with the point light source 36 via the lens 37. When the point light source 36 is lit, part of its light is reflected by the half mirror 30 and heads for the mirror 39, whereby the light is reflected again and returns to the mirror 30. Part of the returning light is transmitted by the half mirror 30, and then forms an image on the imaging surface of the camera 32 via the lens 31. Thus, an image 36' of the fixation target is superposed on the fundus image ER to be displayed on the monitor 50. (The position of the fixation target on the fundus image ER is indicated.)

Figure 2:
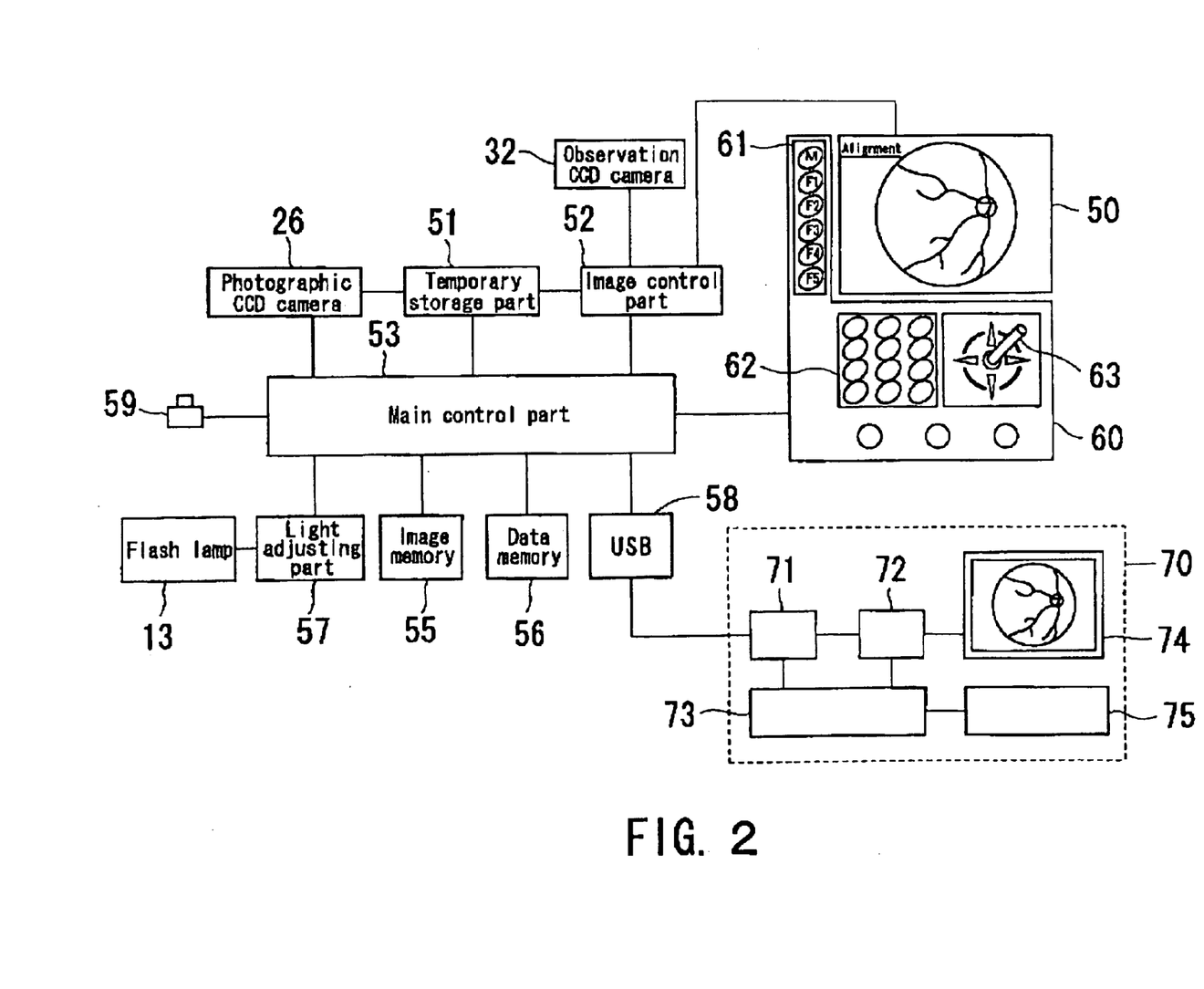
FIG. 2 is a block diagram of primary parts of a control system of the present fundus camera.

FIG. 2 is a block diagram of primary parts of a control system of the present fundus camera. Image signals from the camera 26 are inputted to a temporary storage part 51 and outputted to a monitor 50 through an image control part 52. The image control part 52 controls images displayed on the monitor 50, for example, by selecting between moving images obtained by the camera 32 and a photographed image obtained by the camera 26. A main control part 53 controls the fundus camera comprehensively, and connects to the image control part 52, a photographing switch 59, a light-adjusting part 57 of the flash lamp 13, an image memory 55 such as a PC card, a rewritable data memory 56, a UBS interface 58 performing data communications (sending/receiving data) with an external computer 70, an input part 60, and the like. The input part 60 includes a group of switches 61 which perform different switching functions according to the display on the monitor 50, a ten-digit keypad 62, a lever 63 for inputting operation signals to move a cursor and the like on the monitor 50, and the like.

The external computer 70 includes a storage part 71, an image control part 72, a control part 73, a monitor 74, and an input means 75 such as a keyboard or a mouse.

An image of the eye E illuminated by infrared illumination light from the lamp 10 and through the filter 12 is formed on the imaging surface of the camera 32, and the formed image is displayed on the monitor 50. An examiner performs alignment (position adjustments) of a main body of the fundus camera with respect to the eye E while observing the monitor 50. Also, he moves the lens 23 to achieve proper focus. When he lights the point light source 36, the light is collected into the fundus Ef through the lens 37, the half mirror 30, the return mirror 25, the lens 24, the lens 23, the diaphragm 22, the aperture of the mirror 21, and the lens 20. Thus, an examinee (the eye E) visually identifies the point light source 36 as a fixation target, and a line of sight of the examinee (the eye E) is guided accordingly.

Part of the light emitted from the point light source 36, which has been reflected by the mirror 30, is further reflected by the mirror 39, and the reflected light forms an image on the imaging surface of the camera 32 via the half mirror 30 and the lens 31. As a result, the fixation-target image 36' is displayed on the monitor 50 as well as the fundus image ER.

While observing the fundus image ER and the fixation-target image 36' on the monitor 50, the examiner manipulates the lever 40 to move the point light source 36 to a desired position so that he may observe a desired part of the fundus Ef. When he determines a position for photographing, he presses the switch 59 to perform photographing. When a signal (a trigger signal) from the switch 59 are inputted to the main control part 53, the main control part 53 places the return mirror 25 in the position of the broken lines, and then lights the lamp 13 through the light-adjusting part 57 to illuminate the fundus Ef by the visible illumination light. The visible light reflected from the fundus Ef travels along the optical path of the photographing optical system 2 to enter the imaging surface of the camera 26, so that an image of the fundus Ef is obtained (photographed).

The image photographed by the camera 26 is stored in the temporary storage part 51, and is outputted to the image control part 52, then displayed on the monitor 50. The examiner checks the displayed image, and if it is good enough, he presses an image storage switch included in the switch group 61 to store the photographed image in the image memory 55.

Next, descriptions will be given to photographing images which are to be scaled down and displayed in rows on the monitor 50, and to storing those photographed images.

Figure 3A:
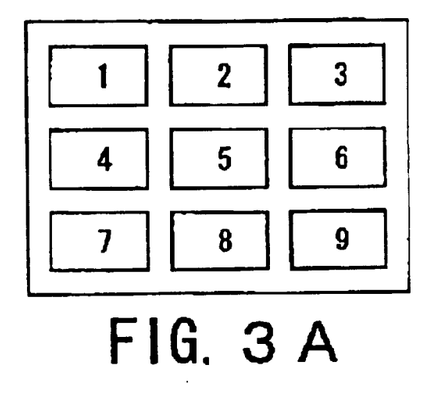
FIGS. 3A to 3D are views showing examples of a template.
Figure 3B:
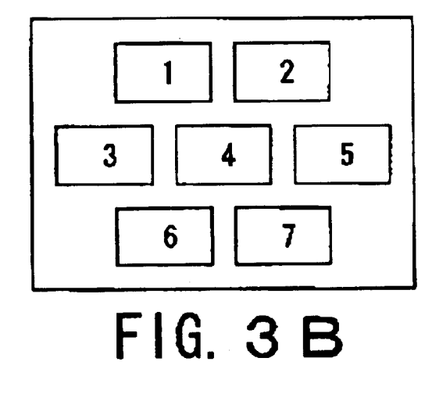
Figure 3C:
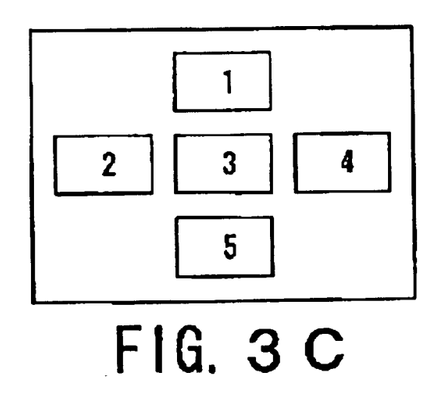
Figure 3D:
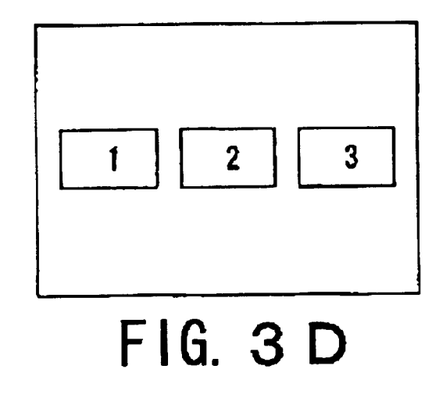

The photographing starts with selecting from among templates for displaying a plurality of scaled-down images in rows on the monitor 50. The switch group 61 is operated to call up a screen for deciding which template to use, and one of the templates is selected. The templates available come in Pattern A (FIG. 3A) with nine of the scaled-down images arranged in grid form, Pattern B (FIG. 3B) with three in the center line and two in each of the upper and lower lines, Pattern C (FIG. 3C) with five arranged in the shape of a cross, and Pattern D (FIG. 3D) with three arranged horizontally. The templates of these patterns are stored in the data memory 56. Hereinafter, description will be given to the case of selecting Pattern B. Incidentally, it is possible that the examiner may create a desired pattern of arrangement as necessary.

After one of the templates is selected, the display on the monitor 50 is shifted to an alignment screen, and the lever 40 is manipulated in the same manner as above to move the point light source 36 for guiding the part to be photographed. When the switch 59 is pressed to perform the photographing, the image photographed by the camera 26 is displayed on the monitor 50. The examiner then checks the displayed image, and if he wants to store it, he presses the image storage switch.

Figure 4:
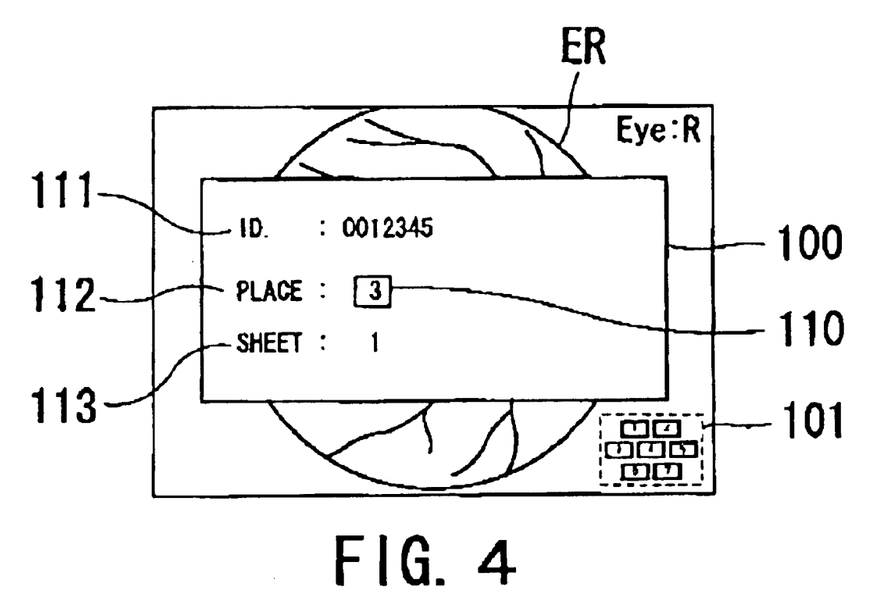
FIG. 4 is a view showing an example of a screen for storing a photographed image.

FIG. 4 shows an example of a storage-setting screen displayed at this point. In the center of the screen of the monitor 50, a storage dialog box 100 appears as it is superposed on the photographed image. In the lower right part of the screen, information 101 concerning the selected template appears simultaneously. The template information 101 includes positional numbers indicating the arrangement of the scaled-down images. The examiner manipulates the lever 63 to shift a cursor 110 shown in the dialog box 100, and enters a patient ID number into an ID field 111. Then, referring to the template information 101, he enters into a PLACE field 112, one of the positional numbers corresponding to a position where he wants the photographed (and scaled-down) image to be displayed. The ID number and the positional number are typed in through the ten-digit keypad 62 (or, by double-clicking a desired positional number in the template information 101). This causes the photographed image to be associated with the position where the image should be arranged in the template (i.e. the photographed image is assigned to one of the arrangement positions in the template). A SHEET field 113 shows the number of sheets; that is, the number of images to which an identical positional number has been assigned in the template information 101. For example, if a positional number 3 in the template information 101 is inputted for two different photographed images, the number of sheets will be indicated as "2".

After those storage-setting data are inputted, a completion switch included in the switch group 61 is pressed, whereby the data concerning the photographed image and those concerning the positional number in the template are stored in the image memory 55 while both data are associated with each other. The main control part 53 treats the type of template and its positional number together as parameters mutually associated to be unique to one image file, in the same manner as with the ID number and information about which of the right or left eye is under photographing (photography).

Following such procedures, desired parts of the fundus Ef are photographed in sequence. After each part is photographed, the positional number in accordance with the template information 101 is inputted to store the photographed image. It should be noted that, in the template displayed at the time of photographing the second image or afterward, a box (or boxes) containing the stored positional number(s) is/are displayed in reverse video. This allows the examiner to recognize which part has not yet been photographed, thereby preventing omission or redundancy during the photographing.

Descriptions will now be given to the case where the images stored in the image memory 55 are scaled down and displayed in rows.

Figure 5:
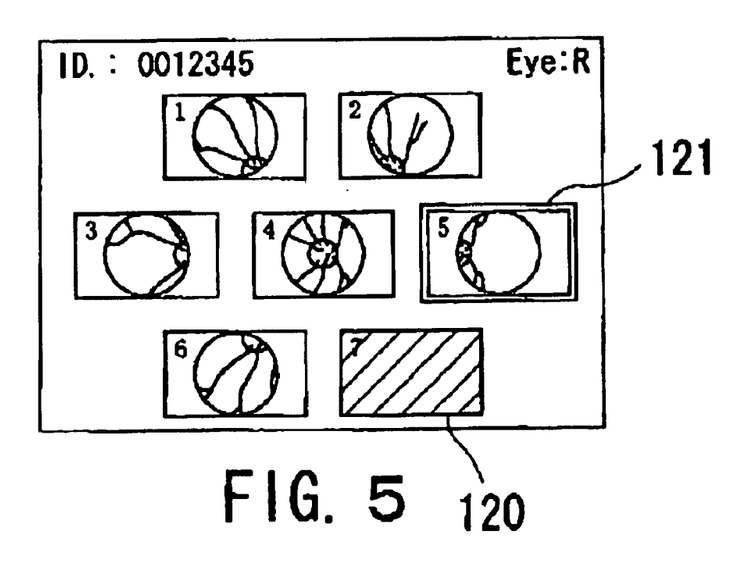
FIG. 5 is a view showing an example of a screen which provides at-a-glance display of a plurality of scaled-down images.

The display of the monitor 50 is shifted to a file-listing screen, on which the examiner specifies an ID number, a right or left eye, and the like. At this point, if he selects at-a-glance display of scaled-down images, as shown in FIG. 5, the monitor 50 provides the at-a-glance display of the scaled-down images in accordance with the arrangement specified in the template information 101. The at-a-glance display is produced by the image control part 52, based on not the sequence of storing the photographed images in the image memory 55, but the type of template stored along with the data on the photographed images and the data on the positional numbers assigned to those images. Such at-a-glance display enables the examiner to interpret the positional relationship among the photographed images and the like as easily as in the case of observing a panoramic composite image.

It should be noted that, in the at-a-glance display of the scaled-down images shown in FIG. 5, a blank 120 indicates that the positional number "7" has not been inputted into any image. Accordingly, it is easy to recognize that a part corresponding to the blank 120 has yet to be photographed. If an image of the part corresponding to the blank 120 is needed, this blank may be filled in by photographing that part, then entering its positional number and storing the image in the same manner as described above.

In addition, the positions in which the photographed (scaled-down) images are arranged are determined (inputted) at the time of storing the images, and the positions are then inputted and stored as positional numbers. Therefore, even if it is required to shift one of the photographed images to any other position after storing that image, the image may be easily shifted in that position by changing its positional number correspondingly. Also, this holds true for changing the type of template.

Descriptions will now be given to the case of redisplaying one of the photographed images (a developed image) on the monitor 50. When one of the scaled-down images is selected using a selecting cursor 121 on the at-a-glance display as shown in FIG. 5, the selected image is brought up, and then the display is changed such that the image is developed to appear in the same fashion as in the display given at the time of photographing. This allows in-depth observation of the photographed part. The lever 63 may be used to shift the selecting cursor 121, and a confirmation switch included in the switch group 61 is pressed to redisplay the developed image. If the same positional number has been inputted to a plurality of photographed images, the display will be stepped through those images with a push of a next-data-selecting switch included in the switch group 61.

Figure 6:
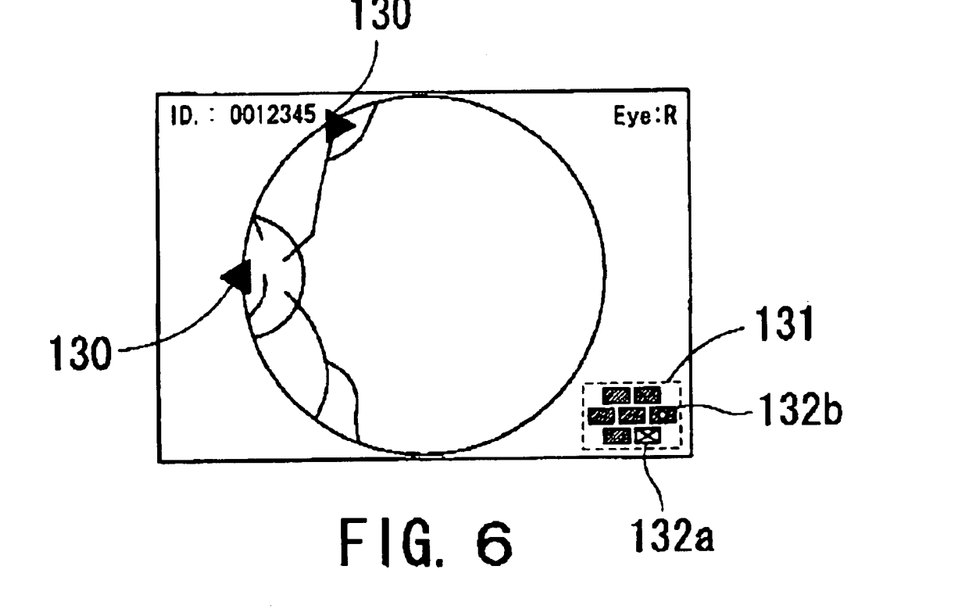
FIG. 6 is a view of an example of a screen which provides redisplay of the photographed image.

FIG. 6 is an example of a screen which provides redisplay of the photographed image (the developed image) During the redisplay of the developed image, if the image memory 55 contains one or more photographed images adjoining the developed image, the screen shows a corresponding number of link marks 130 pointing to the adjoining directions. When one of the link marks 130 is selected using the switch group 61, the screen provides redisplay of the photographed image indicated by the selected link mark as a developed image, without returning to the at-a-glance display of the scaled-down images. In addition, such display of the link marks 130 enables the examiner to confirm the presence of linked images without looking at the at-a-glance display, and to readily interpret the positional relationship among the images. Further, link information 131 illustrating the template for the at-a-glance display of the scaled-down images is superposed on the screen for redisplaying the developed image, and the examiner can thereby review comprehensive positional relationship of the photographed images as well. In the link information 131, a mark 132*b* "○" indicates a position in which the developed image currently on display is arranged, while a mark 132*a* "X" indicates a position (part) for which the photographing has not yet been performed.

It should be noted that the switch group 61 may be used to select between the screen for the at-a-glance display of scaled-down images (FIG. 5) and the screen redisplaying a developed image (FIG. 6). In addition, concerning the scaled-down images appearing on the at-a-glance display, it may be possible to extract from the image memory 55 not only photographed images of the same patient (eye) by designating an ID number, but also photographed images of a particular part (e.g. a papillar or macular spot) of different patients by designating a type of template and a positional number.

In the above descriptions, the monitor 50 included in the fundus camera is used to perform the at-a-glance display of the scaled-down images and the display of the developed image. However, as a matter of course, the monitor 74 of the external computer 70 may also serve for the same purpose. In this case, the data on the photographed images, the type of the template in use, and its positional numbers associated with those images, all of which have been stored in the image memory 55 and the data memory 56, are stored in the storage part 71 of the external computer 70 through the USB interface 58. As in the case with the image control part 52, the image control part 72 controls images displayed on the monitor 74 under input instructions from the input means 75. Further, the present invention is not limited to fundus photographing, and it is also applicable to various kinds of ophthalmic photographing.

As having fully been described up to this point, the present invention facilitates interpretation of the relationship between a photographed image and a position at which the image has been photographed. In addition, it allows photographed images covering large part of a subject to be reviewed through a simple mechanism, thereby facilitating ophthalmic diagnosis.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic photographing apparatus for photographing an eye to be examined, the apparatus comprising:

presenting means for presenting a fixation target onto the eye, the presented fixation target guiding a line of sight of the eye, including sightline moving means for guiding the line of sight of the eye in a different direction;

photographing means for photoelectrically photographing a fundus;

display means for displaying a photographed image;

a memory which stores plural templates for arranging plural scaled-down images of the fundus on a screen of the display means, the plural templates having different arrangement patterns, one template of which is to be selected and used by an operator;

input means for inputting positional information indicating an arrangement position on the selected template for each photographed image in association with the direction of the guided line of sight; and display control means for arranging and displaying plural images based on the selected template and the inputted positional information in a mode for displaying the plural scaled-down images of the fundus and for displaying, when one of the scaled-down images on the screen is selected, the selected image of the fundus as an image on an original scale.

2. The ophthalmic photographing apparatus according to claim 1, wherein the display control means arranges such that information about the selected template appear on the screen.

3. The ophthalmic photographing apparatus according to claim 1, wherein the display control means scales down and arranges the plural images in given positions so that the images appear on the same screen, based on the stored images and their positional information.

4. The ophthalmic photographing apparatus according to claim 3, wherein the display control means arranges such that a specified image and its positional information appear on the same screen, based on specification of one of the plural images displayed on the screen.

5. The ophthalmic photographing apparatus according to claim 1, wherein the display control means arranges such that one of the images and its positional information on appear on the same screen, based on the stored images and their positional information.

6. An ophthalmic photographing apparatus comprising:

a presenting part which presents a fixation target onto an eye to be examined, the presented fixation target guiding a line of sight of the eye, including a sightline moving part which guides the line of sight of the eye in a different direction;

a photographing optical system for photographing a fundus, having a photoelectric photographic element;

a display;

a memory which stores plural templates for arranging plural scaled-down images of the fundus on a screen of the display, the plural templates having different arrangement patterns, one template of which is to be selected and used by an operator;

an input part which inputs positional information indicating an arrangement position on the selected template for each photographed image in association with the direction of the guided line of sight; and a display control part which arranges and displays plural images based on the selected template and the inputted positional information in a mode for displaying the plural scaled-down images of the fundus and for displaying, when one of the scaled-down images on the screen is selected, the selected image of the fundus as an image on an original scale.

\* \* \* \* \*

UNITED STATES PATENT AND TRADEMARK OFFICE
CERTIFICATE OF CORRECTION

PATENT NO. : 6,773,109 B2
DATED : August 10, 2004
INVENTOR(S) : Naoki Ichikawa et al.

It is certified that error appears in the above-identified patent and that said Letters Patent is hereby corrected as shown below:

<u>Title page,</u>
The following should be inserted:
-- (56) References Cited

U.S. PATENT DOCUMENTS

| | | |
|---|---|---|
| 5,374,967 A | 12/1994 | Hideshima et al. |
| 5,912,720 A | 06/1999 | Berger et al. ............351/206 |
| 5,943,116 A | 08/1999 | Zelmer |
| 6,082,859 A | 07/2000 | Okashita et al. |
| 6,224,212 B1 | 05/2001 | Noda et al. ............351/206 |
| 2002/0113939 A1 | 08/2002 | Kitamura ............351/200 |

FOREIGN PATENT DOCUMENTS

| | | |
|---|---|---|
| DE | 43 26 716 A1 | 03/1994 |
| JP | 4-327831 | 11/1992 |
| JP | A 9-173298 | 07/1997 |
| JP | A 11-332832 | 12/1999 |
| JP | A 2000-155788 | 06/2000 |
| JP | A 2000-189387 | 07/2000 |

--

Signed and Sealed this

Nineteenth Day of April, 2005

JON W. DUDAS
*Director of the United States Patent and Trademark Office*